United States Patent [19]

DeNeale et al.

[11] 4,309,404

[45] Jan. 5, 1982

[54] SUSTAINED RELEASE PHARMACEUTICAL COMPOSITIONS

[75] Inventors: Richard J. DeNeale, Willsboro; Paul C. Guley, Plattsburgh; George Milosovich, Rouses Point, all of N.Y.

[73] Assignee: American Home Products Corporation, New York, N.Y.

[21] Appl. No.: 230,154

[22] Filed: Jan. 30, 1981

Related U.S. Application Data

[63] Continuation-in-part of Ser. No. 65,315, Aug. 9, 1979, Pat. No. 4,248,857.

[51] Int. Cl.³ .................. A61K 9/22; A61K 9/32; A61K 9/36
[52] U.S. Cl. .................. 424/21; 424/19; 424/32; 424/33; 424/35
[58] Field of Search .................. 424/19–22, 424/32, 33, 35

[56] References Cited

U.S. PATENT DOCUMENTS

| | | | |
|---|---|---|---|
| 2,991,226 | 7/1961 | Millar et al. | 424/21 |
| 2,993,387 | 7/1961 | Millar et al. | 424/19 |
| 3,018,221 | 1/1962 | Millar et al. | 424/21 |
| 3,074,852 | 1/1963 | Mayron | 424/19 |
| 3,166,476 | 1/1965 | Lowey | 424/19 |
| 3,266,992 | 8/1966 | De Jong | 424/19 |
| 3,279,998 | 10/1966 | Raff et al. | 424/19 |
| 3,458,622 | 7/1969 | Hill | 424/19 |
| 3,558,768 | 1/1971 | Klippel | 424/21 |
| 3,634,584 | 1/1972 | Poole | 424/21 |
| 4,140,756 | 2/1979 | Gallian | 424/21 |

OTHER PUBLICATIONS

West et al., C.A. 85, #103709x, (1976).
Davidson et al., C.A. 85, #198101e, (1976).
ICI, Ltd. C.A. 89, #95008h, (1978).
Dawes et al., C.A. 90, #210054e, (1979).
Aellig C.A. 90, #132966h, (1979).
Tuckman C.A. 90, #142111u, (1979).

*Primary Examiner*—Shep K. Rose
*Attorney, Agent, or Firm*—Mandel Adley F.

[57] ABSTRACT

Novel sustained release compositions comprising a core containing a drug, a seal coating surrounding the core and a sugar coating surround the seal coated core are disclosed.

15 Claims, No Drawings

SUSTAINED RELEASE PHARMACEUTICAL COMPOSITIONS

This is a continuation-in-part of application Ser. No. 65,315, filed Aug. 9, 1979, now allowed, U.S. Pat. No. 4,248,857.

BACKGROUND OF THE INVENTION

1. Field of the Invention

This invention relates to sustained release pharmaceutical compositions and more particularly it relates to sustained release pharmaceutical compositions containing at least one drug in both an inner compressed core and an outer sugar layer.

2. Description of the Related Art

During the past few years there has been much work devoted to the development of systems which promote the release of active ingredients over a prolonged period of time. The advantages of administering orally active drugs in a sustained release formulation are numerous. If a drug is released too quickly in the stomach it can conceivably cause stomach upset. Additionally, the acid environment of the stomach may adversely affect the potency of a drug. Also the taking of medication once a day instead of numerous times a day eliminates a major source of inconvenience for the patient as well as providing for a more even distribution of drug concentration in the blood.

One example for the need for sustained release formulations is in the case of 1-(isopropylamino)-3-(1-naphthyloxy)-2-propanol(propranolol) described in U.S. Pat. No. 3,337,628. This compound is used in the treatment of coronary artery disease, migraine, anxiety, and tremors, and specifically as a $\beta$-adrenergic blocking agent. However, a major drawback of compounds disclosed in U.S. Pat. No. 3,337,628 and particularly propranolol is that because of extensive metabolism, little unchanged active material reaches the systemic circulation after oral administration. Additionally, plasma levels of propranolol show a large patient to patient variation. The preparation of a sustained release formulation containing propranolol would allow for less frequent dosing while achieving similar blood levels to those attained by administering smaller doses more frequently.

U.S. Pat. No. 4,138,475 describes a sustained release composition containing propranolol which consists of a hard gelatine capsule containing film coated spheroids. The present invention relates to a new sustained release composition which is not disclosed in, nor rendered obvious by, either of the above cited patents, nor elsewhere in the art.

SUMMARY OF THE INVENTION

According to the present invention, a sustained release composition is provided comprising a compressed core containing a drug, a seal coating surrounding the compressed core and a sugar coating surrounding the seal-coated, compressed core. In addition to a therapeutically effective amount of the drug, the core further comprises carboxypolymethylene. The seal coating preferably comprises a film coating selected from enteric and nonenteric materials and mixtures thereof, and the sugar coating comprises sugar and a loading dose of at least one drug contained in the core. The sugar coating may further contain additional drugs which are not present in the compressed core.

The compressed core is prepared in admixture and preferably from slugging or dry granulating the drug and other pharmaceutically acceptable excipients and the seal coating may additionally contain a plasticizer. Thus, the core drug or drugs are substantially free of coating within the compressed core itself.

DETAILED DESCRIPTION OF THE INVENTION

The sustained release composition of this invention comprises three main components: a compressed core, a seal coating surrounding the compressed core and a sugar coating surrounding the seal-coated compressed core.

The core formulation comprises drug, carboxypolymethylene, zinc oxide, stearic acid and mannitol, as follows

| Ingredient | Amount by Weight of Core |
|---|---|
| Drug | about 31% to about 53% |
| Carboxypolymethylene | about 7% to about 14.5% |
| Zinc Oxide | about 0% to about 3% |
| Stearic Acid | about 4.5% to about 10% |
| Mannitol | about 3% to about 30% |

The preferred core formulation comprises the following components:

| Ingredient | Amount by Weight of Core |
|---|---|
| Drug | about 33% to about 44% |
| Carboxypolymethylene | about 10% to about 14% |
| Zinc Oxide | about 1% to about 3% |
| Stearic Acid | about 7% to about 10% |
| Mannitol | about 20% to about 30% |

In the core formulation, the ratio of drug to carboxypolymethylene is in the range from about 2.1:1 to about 6.2:1 and preferrably from about 2.5:1 to about 3.7:1. Further the ratio of carboxypolymethylene to zinc oxide is in the range from about 2.2:1 to about 12:1. The core formulation preferably contains up to about 25% microcrystalline cellulose and more particularly about 8% to about 25% by weight of the core.

The carboxypolymethylene (sometimes also referred to as carboxy vinyl polymer) used in this invention is substantially insoluble in water and is the acid form of a polymer prepared as described in U.S. Pat. No. 2,798,053, granted July 2, 1957, selectively utilizing from about 0.75 to 2 percent by weight of polyalkenyl polyether, for example, polyallyl sucrose as the crosslinking material, the remainder being essentially acrylic acid or its equivalent and the polymerization being carried out in a hydrocarbon diluent with a free radical catalyst, for example, benzoyl peroxide. The carboxpolymethylenes employed in this invention are more specifically described in U.S. Pat. No. 2,909,462, of particular interest being the preparation produced in acid form. A particularly effective embodiment of the high molecular weight carboxypolymethylene is a water-soluble polymer of acrylic acid crosslinked with 1% of a polyallyl ether of sucrose having an average of about 5.8 allyl groups for each molecule of sucrose (Carbopol ® 934).

Microcrystalline cellulose is purified, partially depolymerized cellulose prepared by treating alpha cellulose, obtained as a pulp from fibrous plant material, with mineral acids. It is available from FMC corporation under the trade name 'Avicel'. Although Avicel ® pH 101 was used in the present invention, one can use other grades. The employment of microcrystalline cellulose is preferred in the presence of zinc oxide, since, in addition to serving as a compression aid, it appears to facilitate disintegration of the core towards the end of the sustained release dissolution process.

In the core formulation, stearic acid is employed in higher than normal lubricating amounts. It appears that the stearic acid decreases the electrostatic effects of the very fine carboxypolymethylene particles and provides for the necessary flow properties of the formulation during processing.

The mannitol reduces the pH sensitivity of drug release from the core formulation, while the zinc oxide, under neutral to basic conditions, appears to chelate the carboxypolymethylene and slow drug release from the core as the zinc oxide content increases.

The core formulation may further contain other pharmaceutically acceptable excipients such as binders, fillers, compression aids, lubricants, granulation aids, flow aids and the like.

The seal coating is selected from one or more of those film forming materials which is capable of substantially protecting the core during its passage from the stomach to the intestines. Accordingly, depending on the overall properties required by the choice of drug in the composition of this invention, the seal coating may be selected from enteric and nonenteric film forming materials, and mixtures thereof.

The enteric coating materials are materials which are more susceptible to hydrolysis or become soluble at a pH greater than 5. Suitable examples of such materials include polyvinylacetate phthalate (PVAP), cellulose acetate phthalate, carboxymethyl ethyl cellulose, hydroxypropyl methyl cellulose phthalate and the like. In order to minimize hardening of a particular coating (enteric or nonenteric) on aging it is often desirable to employ a plasticizer. In these latter instances the enteric coating material may comprise about 70–100% of the seal coating, and more particularly at least 80% of the seal coating. The seal coating surrounds the compressed core and may be prepared by spray coating the tumbling, compressed cores with a solution of the seal coating.

Nonenteric film forming materials employed in the seal coating are materials which because of their solubility or the amounts (or thicknesses) of the applied coating substantially retard any hydration of the compressed core during its passage through the stomach. For this purpose the seal coating, whether enteric or nonenteric, must cover the entire surface of the compressed core. Nonenteric film forming materials useful for this purpose include a number of hydrocolloids which include one or more, natural, partially or totally synthetic gums. In accordance with the present invention, a preferred nonenteric seal coating includes a mixture of at least two hydrocolloids, one a water soluble polymer and one a water insoluble or relatively insoluble polymer. An example of such a mixture is provided by the use of ethyl cellulose with hydroxypropyl methyl cellulose.

Other nonenteric materials useful in the seal coating include, alkyl celluloses, such as, methylcellulose and propyl cellulose; hydroxy alkyl cellulose, such as, hydroxypropyl cellulose and hydroxyethyl cellulose; and the like.

The amount of seal coating necessary for protecting the core will vary depending on the surface area of the core and the efficiency of the coating equipment and operation. Satisfactory results employing 360 mg. cores have been obtained with as little as about 10 mg. of seal coating to as high as about 30 mg. It is preferred, however, that the seal coating does not add more than about 15–20 mgs. to a 360 mg. core.

The seal coated, compressed cores are then sugar coated with a sugar coating suspension or solution comprising sugar and a loading dose of at least one drug contained in the core, for which sustained release properties are desired. The ratio of said drug in the sugar coating to said drug in the compressed core is in the range from about 1:15 to about 1:3, more particularly from about 1:8 to about 1:6, and preferably about 1:7. In addition to providing fast release of a therapeutically effective amount of drug and while not completely understood, it appears that the loading dose assists in achieving uniform blood levels of the core drug for which sustained release properties are desired. The sugar coating may further contain drugs not contained in the core, for which sustained release properties are not required.

It has been found that the sustained release composition of this invention appear to be more effective at densities greater than about 1.1, preferably a density of at least 1.2 and most preferrably a density of at least 1.3. While not wishing to be bound by any theory, it is believed that the higher densities assist in minimizing stomach emptying times variations among different patients and in maintaining the composition for longer periods in the upper portions of the alimentary tract from which a drug, such as propranolol, is better absorbed.

The composition of this invention provides substantially zero order release of the core contained drug for about 12 hours following the first hour of administration. In the case of the $\beta$-adrenergic blocker, propranolol hydrochloride, the sustained release composition of this invention provides substantially the same therapeutic efficacy for the drug as provided by the identical dosage of drug administered in divided doses, which is the standard dosage regimen.

The composition of this invention is suitable for those drugs having a short half-life (not greater than about 10–12 hours), which therefore may require frequent administration. The composition is especially suitable for water-soluble drugs and particularly for $\beta$-adrenergic blocking agents such as propranolol and its pharmaceutically acceptable acid addition salts. Suitable additional drugs employed in the sugar coating include one or more of those drugs which would be utilized in adjunct therapy with the core drug for which sustained release properties are required. For a $\beta$-adrenergic blocking agent such as propranolol such drugs include diuretics, saluretics vasodilators, alpha beta blockers, ganglionic blockers, centrally acting antihypertensives, inhibitors of the renin-angiotensin-aldosterone system and the like. Illustrative of some of these drugs are hydrochlorothiazide, triamterene, hydralazine, chlorthalidone, furosemide, other thiazide drugs, $\gamma$-[(dimethylamino)methyl]-1,3,4,9-tetrahydro-1-methylpyrano [3,4-b]indole-1-propanol and its pharmaceutically acceptable salts, spiranolactone, captopril, prazocin, isosorbide dinitrate, isosorbide-2-mononitrate, tienilic acid, and the like.

While the present invention is obviously advantageous for acid sensitive drugs and for drugs primarily absorbed from the intestines, it is to be understood that the present invention is not to be construed as being limited to any particular drug (medicament) or class of drugs. Among the various classes of drugs advantageously administered by this invention are, for example, hypertensives, analgesics, inhibitors of aldose reductase, sedatives, antiinflammatory agents, anticonvulsants, adrenergics, vitamins, antihistamines, hypotensives, antitussives, dopamine agonists and the like. Illustrative of some of these drugs are ascorbic acid, aspirin, penicillins, tetracyclines, cephalosporins, metoprolol, pseudoephedrine, chlorpheniramine maleate, 1,8-diethyl-1,3,4,9-tetrahydropyrano[3,4-b]indole-1-acetic acid (known as etodolac), dextromethorphan, primidone, phenylpropanolamine and the like.

The amount of drug contained in the sustained release compositions of this invention will vary depending on the drug or drugs employed. When, for example, the durg is propranolol hydrochloride, the composition of this invention may contain 40–320 mg., more particularly 80–160 mg. and the amount of other drugs when employed in the sugar coating but not the core, will vary according to their therapeutically effective amounts.

The invention is further illustrated but not limited by the following examples.

EXAMPLE 1

Parts by Weight

| Propranolol | 160 | 160 | 160 | 160 | 120 | 120 | 120 | 120 | 120 | 120 | 120 |
|---|---|---|---|---|---|---|---|---|---|---|---|
| Carbopol 934P | 42 | 26 | 36 | 42 | 42 | 40 | 55 | 25.2 | 43.2 | 30.8 | 32 |
| MCC | — | 50 | 60 | 60 | 70 | 70 | 70 | 70 | 70 | 65 | 30 |
| ZnO | — | 5.2 | 3 | 4.5 | 4.5 | 6 | 6 | 11 | 4 | 4.2 | 7.2 |
| Stearic Acid | 35 | 16 | 21 | 24 | 24 | 27 | 27 | 27 | 27 | 24 | 27 |
| Hydroxypropyl Cellulose | — | 8 | — | — | — | — | — | — | — | — | — |
| Mannitol | 106.3 | 58.8 | 17.6 | 10.5 | 37.1 | 114.5 | 99.5 | 104.4 | 83.4 | 33.6 | 86.4 |
| Talc | 1 | 1 | 1 | 1 | 1 | 1 | 1 | 1 | 1 | 1 | 1 |
| Methylcellulose, 15 cps | 5 | — | — | — | — | — | — | — | — | — | — |
| Cabosil ® | 0.7 | 0.6 | 0.6 | 0.6 | 0.6 | 0.5 | 0.5 | 0.4 | 0.4 | 0.4 | 0.4 |
| Ca Stearate | — | 2 | 0.8 | 0.8 | 0.8 | 1 | 1 | 1 | 1 | 1 | 1 |
| PVP | | | | | | | | | 10 | — | 15 |
| Hydroxypropyl Methylcellulose, 10cps | | | | | | | | | | | 40 |

The ingredients were blended until uniform, compressed as slugs, sized, and recompressed into cores of 280–380 mgs.

EXAMPLE 2

The compressed cores of Example 1 are then seal coated with a sufficient amount of the following coating formulation to add approximately 30 mg. to the weight of the compressed cores after drying.

| Polyvinylacetate phthalate (30%) Opaseal ® P-28-0200 | 172ml |
|---|---|
| Methylene Chloride | 410ml |
| Alcohol, Denatured 23 A, Anhydrous | 410ml |
| Acetylated glycerides (Myvacet ® 9-40) | 8.0ml |

EXAMPLE 3

Dried, seal coated cores of (360 mg.) Example 2 are then coated with the following sugar coating suspension containing propranolol hydrochloride in an amount sufficient to add about 20 mg. of the propranolol.

| Microcrystalline Cellulose | .048 kg. |
|---|---|
| Sucrose | .645 kg. |
| Water | .251 kg. |
| Propranolol HCl | .056 kg. |
| Titanium Dioxide | .006 kg. |

The tablets are then further coated with a sugar filler suspension, a sugar smoothing suspension, a sugar color syrup and a polishing suspension. There is thus obtained a sustained release composition containing about 140 mg. of propranolol hydrochloride in the core and 20 mg. of the drug in the sugar coating.

EXAMPLE 4

Sustained release compositions containing both propranolol HCl and hydrochlorothiazide in the sugar coating are prepared employing the following coating formulations and the seal coated cores (360 mg.) of Example 2.

| Sucrose | .515 kg. |
|---|---|
| Propranolol HCl | .053 kg. |
| Hydrochlorothiazide | .133 kg. |
| Calcium Carbonate | .040 kg. |
| Water | .257 kg. |

The tablets are then further coated as in Example 3.

There is thus obtained a sustained release composition of propranolol HCl containing 140 mg. of propranolol HCl in the core and 20 mg. of propranolol HCl with 50 mg. hydrochlorothiazide in the sugar coating.

EXAMPLE 5

The dried, seal coated cores of Example 2 are coated with the following sugar coating suspension and as in Example 3 in an amount sufficient to obtain a sustained release composition containing 140 mg. of propranolol HCl in the core, and containing in the sugar coating 20 mg. propranolol HCl, 50 mg. hydrochlorothiazide, and 100 mg. triamterene.

| Sucrose | .50 kg. |
|---|---|
| Triamterene | .125 kg. |
| Hydrochlorothiazide | .062 kg. |
| Propranolol HCl | .025 kg. |
| Calcium Carbonate | .037 kg. |
| Water | .250 kg. |

EXAMPLE 6

The following sugar coating suspensions are coated onto seal coated cores containing 70 mg. propranolol and 10 mg. in the sugar coating.

| Wt. in kg. | A | B | C |
|---|---|---|---|
| Sucrose | .644 | .533 | .512 |
| Propranolol HCl | .056 | .027 | .012 |
| Hydrochlorothiazide | — | .133 | .062 |
| Triamterene | — | — | .125 |
| Microcrystalline Cellulose | .048 | — | — |
| Titanium Dioxide | .0007 | — | — |
| Calcium Carbonate | — | .040 | .037 |
| Water | .251 | .266 | .250 |

Thus is obtained sustained release compositions containing in the sugar coating:

|  | D | E | F |
|---|---|---|---|
| Propranolol HCl | 10mg | 10mg. | 10mg. |
| Hydrochlorothiazide | — | 50 | 50 |
| Triamterene | — | — | 100 |

EXAMPLE 7

The compressed cores of Examples 1 may also be seal coated with a sufficient amount of either of the following nonenteric coating formulation to add approximately 10-15 mg. to the weight of the compressed cores after dyring.

|  | A | B |
|---|---|---|
| HPMC 50 cps, USP | 17.6 | 6.8 |
| EC 7 cps, NF | 5.1 | 6.8 |
| Stearic Acid USP Purified | 1.3 | 1.4 |
| Solution of Methylene Chloride and 23 A Alcohol | ✓ | ✓ |

These film coated cores may then be further coated as described in Examples 3-6.

What is claimed:

1. A sustained release pharmaceutical composition comprising a compressed core, a seal coating surrounding the core and a sugar coating surrounding the seal coated core wherein,
   (a) the core comprises by weight of the core about 31% to about 53% of the drug, about 7% to about 14.5% carboxypolymethylene, about 0% to about 3% zinc oxide, about 4.5% to about 10% stearic acid and about 3% to about 30% mannitol;
   (b) the seal coating comprises a film coating selected from the group consisting of enteric and non-enteric materials and mixtures thereof; and
   (c) the sugar coating comprises sugar and a loading dose of said drug. and with the proviso that when the seal coating consists essentially of an enteric coating material the drug is other than propranolol or its pharmaceutically acceptable salts.

2. The composition of claim 1 wherein the seal coating comprises an enteric coating material.

3. The composition of claim 1 wherein the seal coating comprises a non-enteric coating material.

4. The composition of claim 1 wherein the ratio of said drug in the core to said carboxypolymethylene is from about 2.1:1 to about 6.2:1; the ratio of carboxypolymethylene to zinc oxide is from about 2.2:1 to about 12:1; and the ratio of said propranolol in the sugar coating to said propranolol in the core is from about 1:15 to about 1:3.

5. The composition of claim 1 or 4 in which the sugar coating further comprises at least one drug used in adjunct therapy with the drug in the core.

6. The composition of claim 4 wherein the core further comprises up to about 25% by weight of microcrystalline cellulose.

7. The composition of claim 5 wherein the core further comprises up to about 25% by weight of microcrystalline cellulose.

8. The composition of claim 1 or 4 wherein the core formulation comprises by weight of the core about 33% to about 44% of said drug; about 10% to about 14% carboxypolymethylene; about 1% to about 3% zinc oxide; about 7% to about 10% stearic acid; about 20% to about 30% mannitol; and up to about 25% microcrystalline cellulose.

9. The composition of claim 2, 3 or 8 wherein the ratio of said drug in the core to said carboxypolymethylene is from about 2.5:1 to about 3.7:1; the ratio of carboxypolymethylene to zinc oxide is from about 2.2:1 to about 12:1; and the ratio of said drug in the sugar coating to said drug in the core is from about 1:6 to about 1:8.

10. The composition of claim 8 or 9 wherein the sugar coating further comprises at least one drug used in adjunct therapy with the drug in the core.

11. The composition of claim 8 or 9 comprising about 40-320 mg. of propranolol hydrochloride.

12. The composition of claim 8 or 9 comprising about 80-160 mg. propranolol hydrochloride.

13. The composition of claim 12 wherein the sugar coating further comprises at least one drug selected from hydrochlorothiazide and triameterene.

14. A sustained release pharmaceutical composition comprising a compressed core containing a drug, a seal coating surrounding the core and a sugar coating surrounding the seal coated core wherein,
   (a) the core comprises by weight of the core about 31% to about 53% of at least one drug, about 7% to about 14.5% carboxypolymethylene; about 0% to about 3% zinc oxide, about 4.5% to about 10% stearic acid and about 3% to about 30% mannitol;
   (b) the seal coating comprises a film coating selected from the group consisting enteric and of non-enteric materials and mixtures thereof; and
   (c) the sugar coating comprises sugar and a loading dose of at least one drug contained in the core; and with the proviso that when the seal coating consists essentially of an enteric coating material the drug is other than propranolol or its pharmaceutically acceptable salts.

15. The composition of claim 14 wherein the sugar coating further comprises at least one drug used in adjunct therapy with a drug contained in the core.

* * * * *